United States Patent
Horlacher

(10) Patent No.: US 11,473,017 B1
(45) Date of Patent: Oct. 18, 2022

(54) PYROLYSIS OIL REACTOR AND PROCESS IMPROVEMENTS FOR ENHANCING PLASTICS RECYCLING

(71) Applicant: CHEVRON PHILLIPS CHEMICAL COMPANY LP, The Woodlands, TX (US)

(72) Inventor: Steven R. Horlacher, League City, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/469,292

(22) Filed: Sep. 8, 2021

(51) Int. Cl.
| | |
|---|---|
| *C10G 1/10* | (2006.01) |
| *C10B 53/07* | (2006.01) |
| *C10G 1/00* | (2006.01) |
| *C10G 9/36* | (2006.01) |
| *C07C 4/04* | (2006.01) |

(52) U.S. Cl.
CPC ............... *C10G 1/10* (2013.01); *C07C 4/04* (2013.01); *C10B 53/07* (2013.01); *C10G 1/002* (2013.01); *C10G 9/36* (2013.01); *C10G 2300/1003* (2013.01); *C10G 2400/20* (2013.01)

(58) Field of Classification Search
USPC .................................................. 585/240–242
See application file for complete search history.

(56) References Cited

U.S. PATENT DOCUMENTS

| | | | | |
|---|---|---|---|---|
| 5,917,102 | A * | 6/1999 | Holighaus | C10B 53/07 208/426 |
| 6,822,126 | B2 * | 11/2004 | Miller | C10G 1/002 208/950 |
| 10,093,860 | B2 * | 10/2018 | Griffiths | C10G 1/10 |
| 10,131,847 | B2 * | 11/2018 | McNamara | C10G 1/10 |
| 2009/0151233 | A1 * | 6/2009 | Miller | C10G 1/10 44/307 |
| 2014/0121426 | A1 * | 5/2014 | Tandon | C10G 1/10 422/187 |
| 2018/0142164 | A1 * | 5/2018 | Boonsawat | C08J 11/10 |
| 2019/0161683 | A1 * | 5/2019 | Narayanaswamy | C10G 69/14 |
| 2019/0177652 | A1 * | 6/2019 | Atkins | C10G 47/16 |
| 2019/0275486 | A1 * | 9/2019 | Peltekis | C08J 11/04 |

(Continued)

FOREIGN PATENT DOCUMENTS

| | | | | |
|---|---|---|---|---|
| WO | WO-2004018592 | A1 * | 3/2004 | C10B 1/06 |
| WO | WO-2014032843 | A1 * | 3/2014 | C10B 11/00 |

(Continued)

*Primary Examiner* — Nina Bhat
(74) *Attorney, Agent, or Firm* — Eversheds Sutherland (US) LLP

(57) ABSTRACT

Described herein are pyrolysis systems and pyrolysis processes for achieving a lighter yield slate than provided in conventional pyrolysis systems. Aspects include: recycling a gaseous pyrolysis product into the pyrolysis reactor to enhance the mixing of the pyrolysis system reactants; installing a bottoms liquid recycle stream to better mix the pyrolysis system reactants; and/or recycling at least a portion of a heavy fraction of the gaseous pyrolysis reactor effluent from a condenser system into the pyrolysis reactor liquid. These improvements can enhance the economic viability of plastic wastes to liquid and gaseous hydrocarbon products which are used for making circular chemical and polymer products.

33 Claims, 1 Drawing Sheet

(56) References Cited

U.S. PATENT DOCUMENTS

2021/0301145 A1\* 9/2021 Gauthier .................. C10G 1/04
2022/0010213 A1\* 1/2022 Sun ......................... C10B 57/06
2022/0098491 A1\* 3/2022 Abbott ................... C10G 45/26

FOREIGN PATENT DOCUMENTS

WO  WO-2018000050 A1 \* 1/2018  ............. B01J 6/008
WO  WO-2021216873 A1 \* 10/2021  ............. C10B 53/07

\* cited by examiner

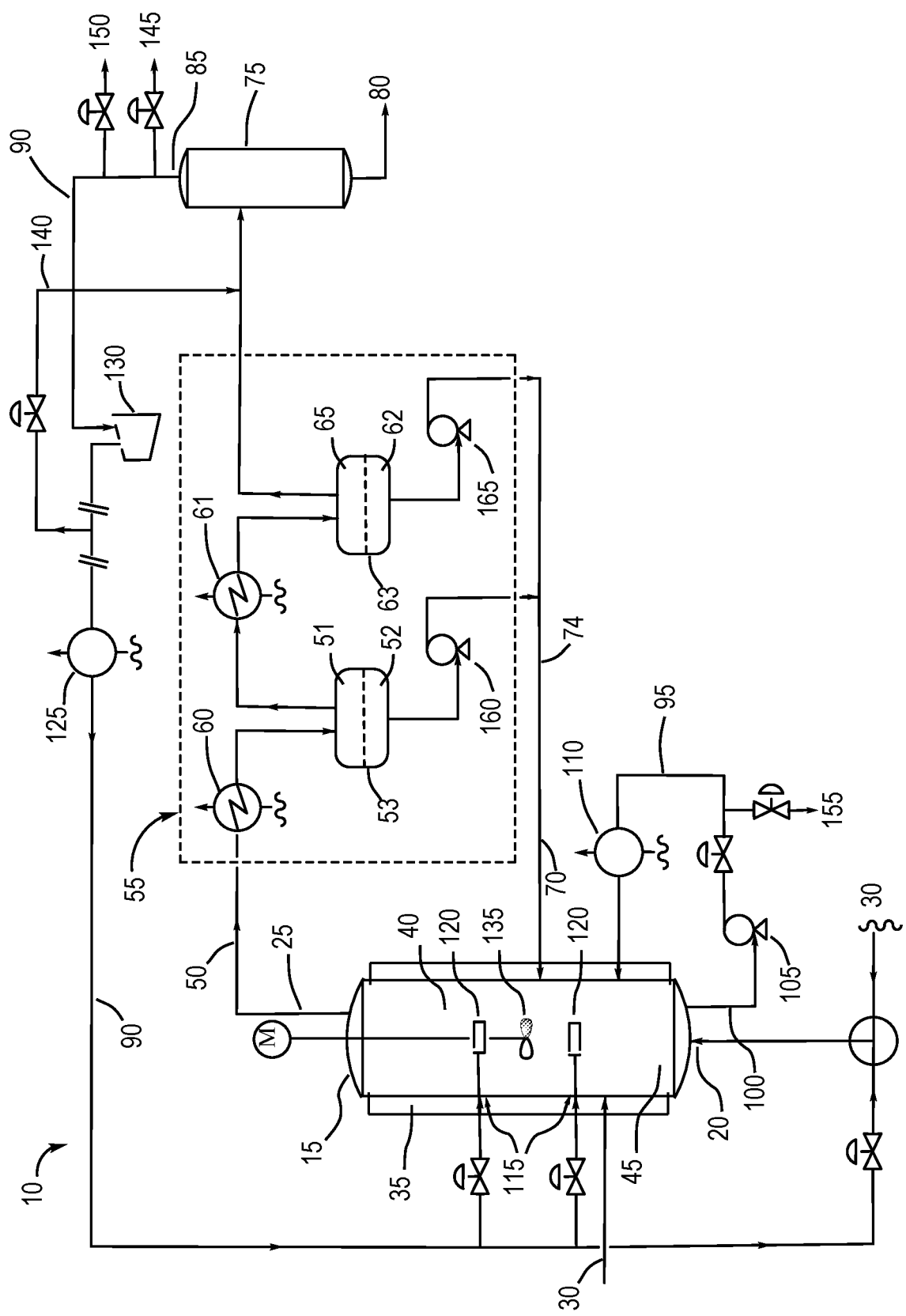

PYROLYSIS OIL REACTOR AND PROCESS IMPROVEMENTS FOR ENHANCING PLASTICS RECYCLING

CROSS REFERENCE TO RELATED APPLICATIONS

None.

TECHNICAL FIELD

This disclosure relates to the production of pyrolysis oil from the pyrolysis of plastic waste which can be used as a feed in the synthesis of chemicals and polymers.

BACKGROUND OF THE DISCLOSURE

The worldwide environmental impact associated with discarded plastic waste products is substantial, therefore the incentive to recycle plastic wastes is pervasive. However, there are significant and persistent problems in conventional recycling methods for plastic products. The melts generated from recycled plastics almost invariably include a range of different types of plastics, which tend to separate into different phases. This phase separation results in structural weakness in the recycled product, and significant proportion of virgin plastic must usually be blended in to impart structural integrity to the product.

An alternative recycling method which is potentially more economically viable is feedstock recycling through the use of pyrolyzed plastic waste materials. Pyrolysis breaks down the polymeric components into products which include an oily, liquid material referred to as pyrolysis oil, which can be recycled in a refinery or chemical plant as a feedstock or co-feedstock for various processing units. One hurdle in using pyrolysis oil in a recycling strategy is achieving improved performance from existing pyrolysis reactors. Conventional pyrolysis reactor designs and operating conditions tend to produce an undesirably high proportion of a heavy waxy fraction, which can require additional processing and increase costs, before the pyrolysis product is suitable as a feed or co-feed in a refinery or chemical plant.

Therefore, what are needed are improved pyrolysis systems and processes for producing pyrolysis oil to be used a feedstock or co-feedstock in a refinery or chemical plant. In particular, improvements in the yield slate from a pyrolysis oil reactor are needed which can improve the proportion of more desirable light products as opposed to the heavy waxy fraction.

SUMMARY OF THE DISCLOSURE

This disclosure provides for new processes and pyrolysis systems for converting plastics such as plastic waste to hydrocarbons, specifically liquid and gaseous pyrolysis reactor products, which subsequently can be used as a feedstock or co-feedstock for making circular products like circular ethylene and polyethylene. Conventionally, pyrolysis reactors are designed to be operated in a fashion that produce a relatively high proportion of heavy waxy products rather than the more desirable and useful lighter products. It has been discovered that an improved yield slate which provides more light products relative to the heavier products can be obtained by modifying and improving upon existing designs of a typical pyrolysis oil reactor.

In one aspect, this disclosure provides pyrolysis systems and processes for achieving a lighter yield slate by improving the mixing of the reactants in a pyrolysis reactor, which can be realized by, for example, systems and methods for recycling gas and liquid effluents from the pyrolysis reactor in specific ways. In one aspect, improved mixing and a lighter yield slate can be attained by introducing a recycled gaseous pyrolysis product into the pyrolysis reactor, through a sparger or distributor if desired, to enhance the mixing of the pyrolysis system reactants. In another aspect, improved mixing and a lighter yield slate can be achieved by installing a bottoms liquid recycle stream with an optional heater, which can better mix the pyrolysis system reactants. These improvements, in turn, can enhance the economic viability of plastic wastes to liquid and gaseous hydrocarbon products, which subsequently can be used for making circular chemical and polymer products.

According to an aspect, this disclosure provides a pyrolysis system for converting plastics to hydrocarbons, the pyrolysis system comprising:
 (a) a pyrolysis reactor comprising (i) an inlet configured to receive a feed, (ii) a pyrolysis reactor liquid including a bottoms liquid, (iii) a first heater configured to heat the pyrolysis reactor liquid, and (iv) an overhead outlet configured to discharge a gaseous pyrolysis reactor effluent;
 (b) a separation system such as a condenser system comprising one or more condensers downstream of the pyrolysis reactor configured to separate the gaseous pyrolysis reactor effluent into a heavy fraction and a light fraction;
 (c) a knock-out drum downstream of the condenser system or other separation system configured to receive the light fraction and separate the light fraction into a light fraction liquid and a light fraction gas; and
 (d) a gas recycle line configured to take off at least a portion of the light fraction gas from the knock-out drum and recycle the light fraction gas into the pyrolysis reactor liquid. The light fraction gas can be compressed downstream of the knock-out drum to recycle the light fraction gas into the pyrolysis reactor liquid.

The gas recycle line can be configured to introduce the light fraction gas into the pyrolysis reactor liquid at one gas inlet location or more than one gas inlet location, which can provide substantial mixing action and improve the yield of light pyrolysis products. The pyrolysis system can further comprise a bottoms liquid recycle line comprising a pump and configured to take off at least a portion of the bottoms liquid from the pyrolysis reactor. This portion of bottoms liquid can be recycled into the pyrolysis reactor liquid.

In a further aspect, this disclosure provides a process for converting plastics to hydrocarbons, the process comprising:
 (a) providing a feed to a pyrolysis reactor;
 (b) pyrolyzing the feed in the pyrolysis reactor to provide (i) a pyrolysis reactor liquid including a bottoms liquid and (ii) a gaseous pyrolysis reactor effluent;
 (c) separating the gaseous pyrolysis reactor effluent into a heavy fraction and a light fraction;
 (d) separating the light fraction of the gaseous pyrolysis reactor effluent into a light fraction liquid and a light fraction gas; and
 (e) recycling at least a portion of the light fraction gas to the pyrolysis reactor, wherein the light fraction gas is introduced into the pyrolysis reactor liquid.

In the above process aspect for converting plastics to hydrocarbons, the step of recycling at least a portion of the light fraction gas to the pyrolysis reactor can include introducing the light fraction gas into the pyrolysis reactor liquid at one gas inlet location or more than one gas inlet location, which can provide the desired mixing action. The process can further include the step of recycling at least a portion of the bottoms liquid from the pyrolysis reactor into the pyrolysis reactor liquid.

These and other aspects, embodiments, and improvements are described more fully in the Detailed Description, the listed Aspects, the claims, and the further disclosure such as the Examples and Drawings provided herein.

BRIEF DESCRIPTION OF THE DRAWINGS

FIG. 1 illustrates aspects of the disclosure showing an exemplary embodiment of a pyrolysis system and process for the production of pyrolysis oil and gas products. In this drawing, the recycling the light fraction gas to the pyrolysis reactor and its introduction into the pyrolysis reactor liquid at more than one gas inlet location are illustrated, which can provide improved mixing action. As illustrated, the process can further include the option of recycling at least a portion of the bottoms liquid from the pyrolysis reactor into the pyrolysis reactor liquid.

DETAILED DESCRIPTION OF THE DISCLOSURE

General Description

Provided in this disclosure are processes, methods, and systems for achieving a higher proportion of lighter hydrocarbon products from a pyrolysis reactor by, among other things, improving the mixing of the reactants in a pyrolysis reactor. Enhanced mixing can be realized by, for example, systems and methods for recycling gas and liquid effluents from the pyrolysis reactor to achieve agitation of the pyrolysis reactor liquid during pyrolysis, such as at a plurality of gas inlet locations at different heights within the pyrolysis reactor. Various recycling systems and methods are disclosed which can bolster the proportion of lighter hydrocarbon products when used individually or in any combination. These improvements can improve the economics of plastic waste recycling for making circular chemical and polymer products.

Definitions

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Unless specified to the contrary, describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example a method can comprise several recited steps (and other non-recited steps) but utilize a catalyst composition preparation consisting of specific steps but utilize a catalyst composition comprising recited components and other non-recited components. While compositions and methods are described in terms of "comprising" various components or steps, the compositions and methods can also "consist essentially of" or "consist of" the various components or steps, unless stated otherwise in the specification or the claims.

The terms "a," "an," and "the" are intended, unless specifically indicated otherwise, to include plural alternatives, e.g., at least one. For instance, the disclosure of "a sparger" is meant to encompass one sparger or more than one sparger unless otherwise specified.

The terms "configured for use" or "adapted for use" and similar language is used herein to reflect that the particular recited structure or procedure is used in an olefin polymerization system or process. For example, unless otherwise specified, a particular structure "configured for use" means it is "configured for use in a pyrolysis reactor system" and therefore is designed, shaped, arranged, constructed, and/or tailored to effect pyrolysis, as would have been understood by the skilled person.

For any particular compound disclosed herein, a general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicant states that one or more steps in the processes disclosed herein can be conducted at a temperature in a range from 10° C. to 75° C., this range should be interpreted as encompassing temperatures in a range from "about" 10° C. to "about" 75° C.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual substituents, analogs, compounds, ligands, structures, or groups thereof, or any members of a claimed group, if for any reason Applicant chooses to claim less than the full measure of the disclosure, for example, to account for a reference or prior disclosure that Applicant may be unaware of at the time of the filing of the application.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means ±15% of the stated value, ±10% of the stated value, ±5% of the stated value, ±3% of the stated value, ±2% of the stated value, or ±1% of the stated value.

The term "olefin" is used herein in accordance with the definition specified by IUPAC: acyclic and cyclic hydrocarbons having one or more carbon-carbon double bonds apart from the formal ones in aromatic compounds. The class "olefins" subsumes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer could be categorized an as ethylene/1-hexene copolymer.

In like manner, the scope of the term "polymerization" includes homopolymerization, copolymerization, terpolymerization, etc. Therefore, a copolymerization process could involve contacting one olefin monomer (e.g., ethylene) and one olefin comonomer (e.g., 1-hexene) to produce a copolymer.

The terms "light fraction" of the gaseous pyrolysis reactor effluent and "heavy fraction" of the gaseous pyrolysis reactor effluent describe the portions of the gaseous pyrolysis reactor effluent which are separated in the separation system such as a condenser system. These terms "light fraction" and "heavy fraction" then refer to portions of the gaseous pyrolysis reactor effluent and are relative terms, and the weight of the hydrocarbons constituting each fraction can depend upon various factors such as the type, the design, and the efficiency of the separation system. These descriptions of light and heavy components are approximate, and the light fraction will include some components found in the heavy fraction, and the heavy fraction will include some components found in the light fraction. However, the vapor or gas products from each condensers and the condenser system of FIG. 1 are richer in the light components than the gaseous pyrolysis reactor effluent feed, and the liquid or condensed products are richer in the heavy products than the gaseous pyrolysis reactor effluent feed. As described further in the Examples, the "light fraction" of the gaseous pyrolysis reactor effluent can constitute primarily $C_{\leq 10}$ hydrocarbons (or $C_{1-10+}$ hydrocarbons), and the "heavy fraction" can constitute primarily $C_{\geq 10}$ hydrocarbons, for example $C_{10-30}$ hydrocarbons.

In a similar fashion, the terms "light fraction gas" and "light fraction liquid" are used to describe the gas portion and the liquid portion, respectively, of the "light fraction" of the gaseous pyrolysis reactor effluent which is fed to and separated by the knock-out drum downstream of the condenser system. These terms are also relative terms, and the weight of the hydrocarbons constituting each portion can depend upon various factors such as the type, the design, and the efficiency of the knock-out drum. However, the "light fraction gas" is richer in the light components than the "light fraction" of the gaseous pyrolysis reactor effluent feed to the knock-out drum, and the "light fraction liquid" is richer in the heavy components than the "light fraction" of the gaseous pyrolysis reactor effluent feed to the knock-out drum. As described further in the Examples, the "light fraction gas" exiting the knock-out drum can constitute approximately $C_1$-$C_5$ hydrocarbons ($C_{\leq 5}$), and the "heavy fraction" can constitute approximately $C_5$-$C_{10}$ hydrocarbons Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Pyrolysis Oil Reactor and Process Improvements

According to an Aspect of this disclosure, there is provided a pyrolysis system for converting plastics to hydrocarbons, the system comprising:

(a) a pyrolysis reactor comprising (i) an inlet configured to receive a feed, (ii) a pyrolysis reactor liquid including a bottoms liquid, (iii) a first heater configured to heat the pyrolysis reactor liquid, and (iv) an overhead outlet configured to discharge a gaseous pyrolysis reactor effluent;

(b) a condenser system comprising one or more condensers downstream of the pyrolysis reactor configured to separate the gaseous pyrolysis reactor effluent into a heavy fraction and a light fraction;

(c) a knock-out drum downstream of the condenser system configured to receive the light fraction and separate the light fraction into a light fraction liquid and a light fraction gas; and (d) a gas recycle line configured to take off at least a portion of the light fraction gas from the knock-out drum, compress the gas, and recycle the light fraction gas into the pyrolysis reactor liquid.

According to a further aspect, this disclosure provides a process for converting plastics to hydrocarbons, the process comprising:

(a) providing a feed to a pyrolysis reactor;

(b) pyrolyzing the feed in the pyrolysis 3 to provide (i) a pyrolysis reactor liquid including a bottoms liquid and (ii) a gaseous pyrolysis reactor effluent;

(c) separating the gaseous pyrolysis reactor effluent into a heavy fraction and a light fraction;

(d) separating the light fraction of the gaseous pyrolysis reactor effluent into a light fraction liquid and a light fraction gas; and (e) compressing and recycling at least a portion of the light fraction gas to the pyrolysis reactor, wherein the light fraction gas is introduced into the pyrolysis reactor liquid.

In an aspect, the pyrolysis system for converting plastics to hydrocarbons can further comprise a bottoms liquid recycle line comprising a pump and configured to take off at least a portion of the bottoms liquid from the pyrolysis reactor and recycle the bottoms liquid into the pyrolysis reactor liquid. This additional step of recycling at least a portion of the bottoms liquid into the pyrolysis reactor liquid can also provide additional mixing efficiency. The bottoms liquid recycle line can further comprise a second heater to heat the bottoms liquid from the pyrolysis reactor prior to recycling the bottoms liquid. By heating the portion of the bottoms liquid being recycled, separation of a recycle liquid that is cooler than the pyrolysis reactor liquid can be reduced or minimized and enhance mixing and further help maintain the operating temperature of the pyrolysis reactor.

In embodiments, the gas recycle line can be configured to introduce the light fraction gas into the pyrolysis reactor liquid at one gas inlet location or at more than one gas inlet location. For example, the gas recycle line can be configured to introduce the light fraction gas into the pyrolysis reactor liquid at a plurality of gas inlet locations, such as 2, 3, 4, 5, 6, 7, 8, 9, or 10 or more gas inlet locations in the pyrolysis reactor liquid. In an aspect, when the gas recycle line introduces the light fraction gas at multiple gas inlet locations in the liquid portion of the pyrolysis reactor, at least some of these multiple gas inlet locations can be situated at different heights within pyrolysis reactor.

In another aspect, the gas recycle line can be configured or further configured to introduce the light fraction gas into the bottoms liquid at one or more than one gas inlet location. Each of these configurations can provide additional mixing efficiency which can help improve the yield slate from the pyrolysis oil reactor to boost the proportion of more desirable light products as opposed to the heavy waxy fraction.

In further aspects, the gas recycle line can comprise or further comprise a sparger or a distributor at the termination of the gas recycle line within the pyrolysis reactor liquid. The sparger or distributor can be employed at some or all of the gas recycle line portions that are used to introduce the light fraction gas into the pyrolysis reactor liquid at multiple gas locations. By sparging or distributing the light fraction gas into the pyrolysis reactor liquid, better mixing efficiency can be achieved.

In embodiments the pyrolysis reactor can further comprise an internal mixer configured to mix the pyrolysis reactor liquid within the pyrolysis reactor. Any type of internal mixer can be utilized in this aspect, for example, a rotary mixer comprising an impeller that is suitable for use in the heated pyrolysis reactor liquid can be employed.

In embodiments, the gas recycle line can comprise or further comprise a third heater to heat the light fraction gas prior to recycling the light fraction gas into the pyrolysis reactor liquid. That is, by including a step of heating the light fraction gas prior to recycling the light fraction gas into the pyrolysis reactor liquid, improved mixing can be achieved. In various aspects, the gas recycle line also can comprise or further comprise a compressor between the knock-out drum and pyrolysis reactor to compress the light fraction gas. Compressing the light fraction gas prior to providing the compressed light fraction gas to the pyrolysis reactor can assist in providing the desired volume flow of light fraction gas to the reactor.

The pyrolysis oil reactor is heated to pyrolyze the plastics feed and provide the hydrocarbons used in further chemical manufacture, and the pyrolysis oil reactor can be heated by any method known in the art. For example, the pyrolysis system for converting plastics to hydrocarbons can include a pyrolysis reactor heater which comprises or is selected from an external heating jacket, a furnace, or any other heating means.

In the disclosed pyrolysis system and process, a condenser system is situated downstream of the pyrolysis reactor, and the condenser system can include one condenser or more than one condenser configured to separate the gaseous pyrolysis reactor effluent into a heavy fraction and a light fraction. For example, the condenser system can include 1, 2, 3, 4 or 5 condensers as desired, depending upon the separation efficiency and the like of the condensers. In an aspect, the condensation can comprise a plurality of condensers, for example, two condensers or three condensers.

When the condenser system comprises a plurality of condensers in series, each can produce a condenser effluent comprising a condensed portion and a gaseous portion, and the gaseous portion of each condenser effluent can transferred to a subsequent condenser in series or to the knock-out drum. While some or all of the gaseous portions from any of the condensers in series can transferred to the knock-out drum, in some embodiments the gaseous portion from only last condenser in series is fed to the knock-out drum. Any gaseous fraction derived from the condenser system which is fed to the knock-out drum can be referred to as the "light fraction" of the gaseous pyrolysis reactor effluent.

In embodiments, separating the light fraction of the gaseous pyrolysis reactor effluent into a light fraction liquid and a light fraction gas can include providing the light fraction of the gaseous pyrolysis reactor effluent to a knock-out drum downstream of the condenser system and separating the light fraction into a light fraction liquid and a light fraction gas.

In another aspect of the disclosure, the pyrolysis reactor can also include a bottom outlet configured to take off bottom char from the pyrolysis reactor. Removing bottom char from the pyrolysis reactor can be carried out continuously or intermittently.

To further improve mixing of the pyrolysis oil reactor contents and to further improve the proportion of light pyrolysis product, the pyrolysis system disclosed herein can further include a heavy fraction recycle line configured to recycle at least a portion of the heavy fraction of the gaseous pyrolysis reactor effluent from the condenser system into the pyrolysis reactor liquid. When the condenser system comprises a plurality of condensers in series, the condensed portion of each condenser effluent can recycled to the pyrolysis oil reactor or can be used for other purposes. Any condensed portion derived from the condenser system or any or all of the condensers in series can be referred to as the heavy fraction of the gaseous pyrolysis reactor effluent and can be recycled to the pyrolysis oil reactor.

The heavy fraction recycle line can include a pump configured to recycle the heavy fraction of the gaseous pyrolysis reactor effluent back to the pyrolysis reactor. Thus, the disclosed process can further include the step of recycling at least a portion of the heavy fraction of the gaseous pyrolysis reactor effluent into the pyrolysis reactor liquid.

Pyrolysis Oil Reactor and Process Conditions

According to an aspect, in the disclosed process for converting plastics to hydrocarbons the pyrolysis oil reactor feed can comprise, consist of, consist essentially of, or can be selected from a plastics feed. For example, the pyrolysis oil reactor feed can comprise or can be selected from a waste plastics feed. In an aspect, the pyrolysis oil reactor feed can be provided to the pyrolysis reactor from an extruder or a liquefier.

The pyrolysis reactor feed and the resulting pyrolysis reactor effluent (such as the gaseous pyrolysis reactor effluent) can be derived from the pyrolysis of a wide range of plastic wastes. For example, the pyrolysis reactor effluent can be derived from pyrolysis of polyolefins of any type such as polyethylene and polypropylene polymers and co-polymers, polystyrene, polyethylene terephthalate (PET), polyvinyl chloride (PVC), polyamides, polycarbonates, polyurethanes, polyesters, copolymers thereof, filled polymers thereof, composites thereof, natural or synthetic rubber, tires, or any combination thereof. For example, the plastic waste in the pyrolysis reactor feed can comprise polyethylene, polypropylene, polystyrene, polyethylene terephthalate (PET), polyamide, polycarbonate, polyurethane, or polyester.

In some processes, it may be desirable for the pyrolysis reactor effluent (such as the gaseous pyrolysis reactor effluent) to have relatively low concentrations of chloride, which can be accomplished by, for example, selecting plastic wastes having low concentrations of chloride-containing polymers such as PVC. In another aspect, using pyrolysis reactor effluent having relatively low concentrations of chloride may also be accomplished by purification of the pyrolysis reactor effluent prior to routing it to a condensation unit, a knock-out drum, or any downstream unit as a feed or a co-feed. In still a further aspect, the plastic waste can comprise a chloride-containing polymer, at least a portion of which has been removed from the plastic waste prior to pyrolyzing the plastic waste in the pyrolysis unit.

In embodiments, the gaseous pyrolysis reactor effluent can contain a range of non-hydrocarbon contaminants. For example, the pyrolysis reactor effluent may contain a non-hydrocarbon contaminant that comprises or is selected from an inorganic acid, an organic acid, a binary compound of a group 15 element and hydrogen, a binary compound of a group 16 element and hydrogen, an organic compound comprising a group 15 element, or an organic compound comprising a group 16 element. Examples of non-hydrocarbon contaminant that may occur in the pyrolysis reactor effluent include but are not limited to HCl, HBr, phosphine, arsine, stibine, an alcohol, an organic acid, a nitrogen oxide, chloroform, a $C_1$-$C_3$ hydrocarbon chloride, or a $C_1$-$C_3$ hydrocarbon fluoride. In embodiments, the gaseous pyrolysis reactor effluent can be pretreated with caustic, an amine, a metal oxide such as zinc oxide, calcium oxide, or iron oxide, a molecular sieve, or a promoted or activated alumina prior to feeding the gaseous pyrolysis reactor effluent to the condenser system.

In another aspect, the pyrolysis reactor feed can comprise or can be selected from a plastics feed, wherein the plastics feed can be pretreated to remove acid contaminants prior to being provided to the pyrolysis reactor. In this aspect, the plastics feed can be pretreated with caustic, an amine, a zinc alkyl compound, a group II metal, or a combination thereof prior to being provided to the pyrolysis reactor. Another aspect provides that the plastics feed can be processed through a thin film evaporator to remove volatile acid components prior to being provided to the pyrolysis reactor.

According to an aspect, the plastics feed can be provided to the pyrolysis reactor at any temperature or temperature range that is suitable for the specific pyrolysis reactor and process. For example, the plastics feed can be provided to the pyrolysis reactor at a temperature of from about 300° F. to about 400° F., or temperatures outside this range. In one aspect, the plastics feed can be heated to a temperature of about 300° F., about 310° F., about 320° F., about 330° F., about 340° F., about 350° F., about 360° F., about 370° F., about 380° F., about 390° F., or about 400° F., or even higher, prior to being fed to the pyrolysis reactor.

The pyrolysis reactor itself can be operated at any temperature or temperature range that is suitable for the specific pyrolysis reactor and process. For example, the pyrolysis reactor can be operated at temperatures ranging from about 900° F. to about 1,100° F., or temperatures outside this range. In one aspect, the pyrolysis reactor can be operated at a temperature of about 900° F., about 925° F., about 950° F., about 975° F., about 1,000° F., about 1,025° F., about 1,050° F., about 1,075° F., or about 1,100° F., or even higher. Thus, in an aspect, the gaseous pyrolysis reactor effluent can be discharged from the pyrolysis reactor at a temperature of from about 900° F. to about 1,100° F.

According to further aspects of the disclosure, the process for converting plastics to hydrocarbons can include the further step of providing the light fraction liquid from the light fraction of the gaseous pyrolysis reactor effluent to a steam cracker furnace to produce a stream cracker furnace effluent comprising ethylene, propylene, and light ($C_2$-$C_3$) saturated hydrocarbons. In this aspect, the stream cracker furnace effluent can be subsequently separated to provide products for further use downstream in a circular process. For example, the stream cracker furnace effluent can be subsequently separated to provide an ethylene stream. This ethylene stream or a portion thereof can be fed to a downstream polymerization reactor of any type to form circular polyethylene. Because the process and system for improving the operation of a pyrolysis oil reactor is applicable to any process that uses a pyrolysis oil or a pyrolysis gas to make chemicals and polymers, the disclosed process and system can be used to boost the efficiency of a circular chemical process and accordingly enhance the fraction of circular chemicals generated in a circular chemical process.

EXAMPLES

The present disclosure is further illustrated by the following examples, which are not to be construed in any way as imposing limitations upon the scope of the invention. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims.

EXAMPLE 1

FIG. 1 illustrates one exemplary embodiment of the pyrolysis system of this disclosure. According to FIG. 1, the pyrolysis system 10 for converting plastics to hydrocarbons includes a pyrolysis reactor 15 having a feed inlet 20 configured to receive a pyrolysis reactor feed 30, and an overhead outlet 25 configured to discharge a gaseous pyrolysis reactor effluent 50 therethrough. In the FIG. 1 embodiment, pyrolysis reactor 15 includes a first heater 35 in the form of an external heating jacket. Pyrolyzing the reactor feed 30 in pyrolysis reactor 15 provides a pyrolysis reactor liquid 40 including a bottoms liquid 45 and the gaseous pyrolysis reactor effluent 50.

The FIG. 1 embodiment also features a bottoms liquid recycle line 95 which is configured to remove a portion of the bottoms liquid 45 through bottom outlet 100 of the pyrolysis reactor 15 and which includes a pump 105 and a second heater 110. Bottoms liquid recycle line 95 is configured to recycle the bottoms liquid 45 into the pyrolysis reactor liquid 40. A bottoms liquid take-off 155 allows withdrawing bottoms liquid for various applications such as in asphalt manufacture.

In this embodiment of FIG. 1, an internal mixer 135 is also shown, which further improves the mixing of the pyrolysis reactor liquid 40 and thereby improve the product slate to boost the proportion of light product.

Separating the gaseous pyrolysis reactor effluent 50 is achieved at the condenser system 55, which can comprise one or more than one condensers downstream of the pyrolysis reactor 15. The FIG. 1 condenser system 55 is shown to include two condensers 60 and 61. Regardless of the number of condensers, the condenser system 55 is configured to separate the gaseous pyrolysis reactor effluent 50 into a heavy fraction 70 and a light fraction 65.

The final gaseous effluent from the condenser system 55 which is supplied to the downstream knock-out drum 75 is termed the light fraction 65, and the combination of any liquids condensed from the condenser system 55 is termed the heavy fraction 70. In this aspect, the light fraction 65 can constitute the vapor product which is not condensed by the condenser system 55 and which is supplied to the downstream knock-out drum 75, and heavy fraction 70 can constitute the total product that is condensed by the condenser system 55.

The FIG. 1 embodiment is shown with two condensers in series, 60 and 61, in which the first condenser 60 separates the gaseous pyrolysis reactor effluent 50 into a first condenser liquid 52, which is collected in a first receiver 53, and a first condenser vapor 51. In one aspect, the first condenser vapor 51 can comprise primarily $C_{\leq 10}$ hydrocarbons (or $C_{1-10+}$ hydrocarbons), and the first condenser liquid 52 can comprise primarily $C_{24\ 10}$ hydrocarbons, for example, $C_{10-30}$ hydrocarbons. In an aspect, the first condenser vapor 51 can include some $C_{>10}$ hydrocarbons and the first condenser liquid 52 can include some $C_{\leq 10}$ hydrocarbons.

When the $C_{1-10+}$ hydrocarbon-containing first condenser vapor 51 is routed to and further separated at the second condenser 61, a second condenser vapor and a second condenser liquid 62 which is collected in a second receiver 63 are provided. In this embodiment, the second condenser vapor is the final vapor product which is not condensed and therefore constitutes the light fraction 65 of the gaseous pyrolysis reactor effluent which is routed to the knock-out drum. In an aspect, the second condenser vapor can comprise primarily $C_{\leq 5}$ hydrocarbons ($C_{1-5}$ hydrocarbons), and the second condenser liquid 62 can comprise primarily $C_{5-10+}$ hydrocarbons, for example, both the second condenser vapor 65 and the second condenser liquid 62 can include $C_5$ products. These descriptions of light and heavy components are approximate, but the vapor or gas products from the condensers and the condenser system of FIG. 1 are richer in the light components than the feed, and the liquid or condensed products are richer in the heavy products than the feed.

In some aspects, the first condenser liquid 52 can comprise a distillate component and waxy component in the 450° F. to 1,100° F. distillation range, and second condenser liquid 62 can comprise a gasoline or naphtha distillate in the 70° F. to 450° F. distillation range. The first condenser liquid 52 or the second condenser liquid 62 or both can be further separated, returned to the pyrolysis reactor, or used in other processes in any blends with other products or each other, or stored for other uses. For example, FIG. 1 illustrates an embodiment of a condenser liquid return line 74 which returns the first condenser liquid 52 via second pump 160 and the second condenser liquid 62 via third pump 165 to the pyrolysis reactor 15, although either the first condenser liquid 52 only or the second condenser liquid 62 only could be returned if desired.

Knock-out drum 75 is situated downstream of the condenser system 55 and is configured to receive the light fraction 65 from the condenser system and separate this light fraction into a light fraction liquid 80 and a light fraction gas 85. An overhead gas recycle line 90 is configured to take off at least a portion of the light fraction gas 85 from knock-out drum 75 and compress and recycle the light fraction gas 85 into the pyrolysis reactor liquid 40 with the aid of a compressor 130. Some of light fraction gas 85 can be diverted to fuel 145 or sent to flare 150 if needed or desired.

Recycling the light fraction gas 85 to the pyrolysis reactor 15 occurs through at least one gas inlet 115, shown in FIG. 1. Two gas inlets 115 are illustrated in this embodiment, which terminate at different heights within the pyrolysis reactor liquid through a sparger 120 or a distributor. If desired, the gas recycle line 90 can include a third heater 125 downstream of the compressor to heat the light fraction gas 85 prior to recycling. Gas recycle line 90 can further include a gas kickback line 140 which can recycle some of the light fraction gas 85 from the gas recycle line 90 into the light fraction feed 65 to the knock-out drum 75 to protect the compressor.

Therefore, FIG. 1 illustrates an embodiment for providing substantially increased mixing to the pyrolysis oil reactor contents during operation, thereby improving the product slate to boost the proportion of light product. Example 1 and FIG. 1 are not intended to be limiting, as all the components and processes depicted in FIG. 1 are not necessary, and additional separations and routing of various products can be employed.

EXAMPLE 2

Another example of an embodiment of the pyrolysis system is set out below. In this Example, the pyrolysis system for converting plastics to hydrocarbons, can comprise:
(a) a pyrolysis reactor comprising an inlet to receive a feed, a pyrolysis reactor liquid including a bottoms liquid, a first heater configured to heat the pyrolysis reactor liquid, and an overhead outlet configured to discharge a gaseous pyrolysis reactor effluent;
(b) a condenser system comprising a plurality of condensers in series downstream of the pyrolysis reactor configured to separate the gaseous pyrolysis reactor effluent into a heavy fraction and a light fraction;
(c) a knock-out drum downstream of the condenser system configured to receive the light fraction and separate the light fraction into a light fraction liquid and a light fraction gas; and
(d) a gas recycle line from the knock-out drum to the pyrolysis reactor, the gas recycle line comprising a compressor and configured to take off at least a portion of the light fraction gas from the knock-out drum and introduce the compressed light fraction gas through a sparger or a distributor into the pyrolysis reactor liquid at a plurality of gas inlet locations at different heights within pyrolysis reactor.

EXAMPLE 3

Still another example of an embodiment of the process for converting plastics to hydrocarbons is set out below. In this Example, the process for converting plastics to hydrocarbons can comprise:
(a) providing a plastics feed to a pyrolysis reactor;
(b) pyrolyzing the plastics feed in the pyrolysis reactor to provide (i) a pyrolysis reactor liquid including a bottoms liquid and (ii) a gaseous pyrolysis reactor effluent;
(c) providing the gaseous pyrolysis reactor effluent to a condenser system comprising a plurality of condensers downstream of the pyrolysis reactor and separating the gaseous pyrolysis reactor effluent into a heavy fraction and a light fraction;
(d) providing the light fraction of the gaseous pyrolysis reactor effluent to a knock-out drum downstream of the condenser system and separating the light fraction into a light fraction liquid and a light fraction gas; and
(e) compressing and recycling at least a portion of the light fraction gas to the pyrolysis reactor, wherein the compressed light fraction gas is introduced through a sparger or a distributor into the pyrolysis reactor liquid at a plurality of gas inlet locations at different heights within pyrolysis reactor.

ASPECTS OF THE DISCLOSURE

The invention is described above with reference to numerous aspects, embodiments, and specific examples. Many variations will suggest themselves to those skilled in the art in light of the above detailed description. All such obvious variations are within the full intended scope of the appended claims. Other aspects of the invention can include, but are not limited to, the following. Aspects which are described as "comprising" certain components or steps, may also "consist essentially of" or "consist of" those components or steps, unless stated otherwise.

Aspect 1. A pyrolysis system for converting plastics to hydrocarbons, the system comprising:
(a) a pyrolysis reactor comprising an inlet configured to receive a feed, a pyrolysis reactor liquid including a bottoms liquid, a first heater configured to heat the pyrolysis reactor liquid, and an overhead outlet configured to discharge a gaseous pyrolysis reactor effluent;
(b) a condenser system comprising one or more condensers downstream of the pyrolysis reactor configured to separate the gaseous pyrolysis reactor effluent into a heavy fraction and a light fraction;
(c) a knock-out drum downstream of the condenser system configured to receive the light fraction from the condenser system and separate the light fraction into a light fraction liquid and a light fraction gas; and
(d) a gas recycle line configured to take off at least a portion of the light fraction gas from the knock-out drum and recycle the light fraction gas into the pyrolysis reactor liquid.

Aspect 2. The pyrolysis system for converting plastics to hydrocarbons according to Aspect 1, wherein the pyrolysis system further comprises a bottoms liquid recycle line comprising a first pump and configured to take off at least a portion of the bottoms liquid from the pyrolysis reactor and recycle the bottoms liquid into the pyrolysis reactor liquid.

Aspect 3. The pyrolysis system for converting plastics to hydrocarbons according to Aspect 2, wherein the bottoms liquid recycle line further comprises a second heater to heat the bottoms liquid from the pyrolysis reactor prior to recycling the bottoms liquid into the pyrolysis reactor liquid.

Aspect 4. The pyrolysis system for converting plastics to hydrocarbons according to any of Aspects 1-3, wherein the gas recycle line is configured to introduce the light fraction gas into the pyrolysis reactor liquid at one gas inlet location or more than one gas inlet location.

Aspect 5. The pyrolysis system for converting plastics to hydrocarbons according to any of Aspects 1-3, wherein the gas recycle line is configured to introduce the light fraction gas into the pyrolysis reactor liquid at a plurality of gas inlet locations.

Aspect 6. The pyrolysis system for converting plastics to hydrocarbons according to Aspect 5, wherein the plurality of gas inlet locations within the pyrolysis reactor liquid are situated at different heights within the pyrolysis reactor.

Aspect 7. The pyrolysis system for converting plastics to hydrocarbons according to any of the preceding Aspects, wherein the gas recycle line is configured or further configured to introduce the light fraction gas into the bottoms liquid.

Aspect 8. The pyrolysis system for converting plastics to hydrocarbons according to any of the preceding Aspects, wherein the gas recycle line comprises or further comprises a sparger or a distributor at the termination of the gas recycle line within the pyrolysis reactor liquid.

Aspect 9. The pyrolysis system for converting plastics to hydrocarbons according to any of the preceding Aspects, wherein the gas recycle line comprises or further comprises a third heater to heat the light fraction gas prior to recycling the light fraction gas into the pyrolysis reactor liquid.

Aspect 10. The pyrolysis system for converting plastics to hydrocarbons according to any of the preceding Aspects, wherein the gas recycle line comprises or further comprises a compressor between the knock-out drum and pyrolysis reactor to compress the light fraction gas.

Aspect 11. The pyrolysis system for converting plastics to hydrocarbons according to any of Aspects 1-10, wherein the first heater comprises or is selected from an external heating jacket.

Aspect 12. The pyrolysis system for converting plastics to hydrocarbons according to any of Aspects 1-10, wherein the first heater comprises or is selected from a furnace.

Aspect 13. The pyrolysis system for converting plastics to hydrocarbons according to any of the preceding Aspects, wherein the pyrolysis reactor further comprises an internal mixer configured to mix the pyrolysis reactor liquid within the pyrolysis reactor.

Aspect 14. The pyrolysis system for converting plastics to hydrocarbons according to any of the preceding Aspects, wherein the condenser system comprises a plurality of condensers.

Aspect 15. The pyrolysis system for converting plastics to hydrocarbons according to any of the preceding Aspects, wherein the condenser system comprises a plurality of condensers in series and the heavy fraction of the gaseous pyrolysis reactor effluent comprises at least one condensation product of the plurality of condensers.

Aspect 16. The pyrolysis system for converting plastics to hydrocarbons according to any of the preceding Aspects, wherein the pyrolysis reactor further comprises a bottom outlet configured to take off bottom char from the pyrolysis reactor continuously or intermittently.

Aspect 17. The pyrolysis system for converting plastics to hydrocarbons according to any of the preceding Aspects, wherein the pyrolysis system further comprises a heavy fraction recycle line comprising a second pump and configured to recycle at least a portion of the heavy fraction of the gaseous pyrolysis reactor effluent from the condenser system into the pyrolysis reactor liquid.

Aspect 18. A process for converting plastics to hydrocarbons, the process comprising:
(a) providing a feed to a pyrolysis reactor;
(b) pyrolyzing the feed in the pyrolysis reactor to provide (i) a pyrolysis reactor liquid including a bottoms liquid and (ii) a gaseous pyrolysis reactor effluent;
(c) separating the gaseous pyrolysis reactor effluent into a heavy fraction and a light fraction;
(d) separating the light fraction of the gaseous pyrolysis reactor effluent into a light fraction liquid and a light fraction gas; and
(e) recycling at least a portion of the light fraction gas to the pyrolysis reactor, wherein the light fraction gas is introduced into the pyrolysis reactor liquid.

Aspect 19. The process for converting plastics to hydrocarbons according to Aspect 18, the process further comprising the step of recycling at least a portion of the bottoms liquid from the pyrolysis reactor into the pyrolysis reactor liquid.

Aspect 20. The process for converting plastics to hydrocarbons according to Aspect 19, wherein the step of recycling at least a portion of the bottoms liquid further comprises heating the bottoms liquid prior to recycling into the pyrolysis reactor liquid.

Aspect 21. The process for converting plastics to hydrocarbons according to any of Aspects 18-20, wherein the step of recycling at least a portion of the light fraction gas to the pyrolysis reactor comprises introducing the light fraction gas into the pyrolysis reactor liquid at one gas inlet location or more than one gas inlet location.

Aspect 22. The process for converting plastics to hydrocarbons according to any of Aspects 18-20, wherein the step of recycling at least a portion of the light fraction gas to the pyrolysis reactor comprises introducing the light fraction gas into the pyrolysis reactor liquid at a plurality of gas inlet locations.

Aspect 23. The process for converting plastics to hydrocarbons according to Aspect 22, wherein the plurality of gas inlet locations within the pyrolysis reactor liquid are situated at different heights within pyrolysis reactor.

Aspect 24. The process for converting plastics to hydrocarbons according to any of Aspects 18-23, wherein the step of recycling at least a portion of the light fraction gas to the pyrolysis reactor comprises or further comprises introducing the light fraction gas into the bottoms liquid.

Aspect 25. The process for converting plastics to hydrocarbons according to any of Aspects 18-24, wherein the step of recycling at least a portion of the light fraction gas to the pyrolysis reactor further comprises sparging or distributing the light fraction gas into the pyrolysis reactor liquid.

Aspect 26. The process for converting plastics to hydrocarbons according to any of Aspects 18-25, further comprising the step of heating the light fraction gas prior to recycling the light fraction gas into the pyrolysis reactor liquid.

Aspect 27. The process for converting plastics to hydrocarbons according to any of Aspects 18-26, further comprising the steps of compressing the light fraction gas prior to providing the compressed light fraction gas to the pyrolysis reactor.

Aspect 28. The process for converting plastics to hydrocarbons according to any of Aspects 18-27, wherein the step of pyrolyzing the feed comprises heating the pyrolysis reactor with an external heating jacket.

Aspect 29. The process for converting plastics to hydrocarbons according to any of Aspects 18-27, wherein the step of pyrolyzing the feed comprises heating the pyrolysis reactor with a furnace.

Aspect 30. The process for converting plastics to hydrocarbons according to any of Aspects 18-29, wherein the process further comprises the step of mixing the pyrolysis reactor liquid within the pyrolysis reactor.

Aspect 31. The process for converting plastics to hydrocarbons according to Aspect 30, wherein the step of mixing is carried out with an internal mixer.

Aspect 32. The process for converting plastics to hydrocarbons according to any of Aspects 18-31, wherein the step of separating the gaseous pyrolysis reactor effluent comprises providing the gaseous pyrolysis reactor effluent to a condenser system comprising one or more condensers.

Aspect 33. The process for converting plastics to hydrocarbons according to Aspect 32, wherein the condenser system comprises a plurality of condensers.

Aspect 34. The process for converting plastics to hydrocarbons according to any of Aspects 18-31, wherein the step of separating the gaseous pyrolysis reactor effluent comprises providing the gaseous pyrolysis reactor effluent to a condenser system comprising a plurality of condensers in series, and the heavy fraction of the gaseous pyrolysis reactor effluent comprises at least one condensation product of the plurality of condensers.

Aspect 35. The process for converting plastics to hydrocarbons according to any of Aspects 18-34, wherein the step of separating the light fraction of the gaseous pyrolysis reactor effluent into a light fraction liquid and a light fraction gas comprises providing the light fraction of the gaseous pyrolysis reactor effluent to a knock-out drum downstream of the condenser system and separating the light fraction into a light fraction liquid and a light fraction gas.

Aspect 36. The process for converting plastics to hydrocarbons according to any of Aspects 18-35, further comprising the step of removing bottom char from the pyrolysis reactor continuously or intermittently.

Aspect 37. The process for converting plastics to hydrocarbons according to any of Aspects 18-36, further comprising the step of recycling at least a portion of the heavy fraction of the gaseous pyrolysis reactor effluent into the pyrolysis reactor liquid.

Aspect 38. The process for converting plastics to hydrocarbons according to any of Aspects 18-37, wherein the feed is provided to the pyrolysis reactor at a temperature of from about 300° F. to about 400° F.

Aspect 39. The process for converting plastics to hydrocarbons according to any of Aspects 18-38, wherein the gaseous pyrolysis reactor effluent is discharged from the pyrolysis reactor at a temperature of from about 900° F. to about 1,300° F.

Aspect 40. The process for converting plastics to hydrocarbons according to any of Aspects 18-39, further comprising the step of providing the light fraction liquid from the light fraction of the gaseous pyrolysis reactor effluent to a steam cracker furnace to produce a stream cracker furnace effluent comprising ethylene, propylene, and light ($C_1$-$C_5$) saturated hydrocarbons.

Aspect 41. The process for converting plastics to hydrocarbons according to Aspect 40, further comprising the step of separating the steam cracker furnace effluent to provide an ethylene stream.

Aspect 42. The process for converting plastics to hydrocarbons according to Aspect 41, further comprising the step of feeding at least a portion of the ethylene stream to a polymerization reactor to form polyethylene.

Aspect 43. The pyrolysis system or the process for converting plastics to hydrocarbons according to any of the preceding Aspects, wherein the feed comprises or is selected from a plastics feed.

Aspect 44. The pyrolysis system or the process for converting plastics to hydrocarbons according to any of the preceding Aspects, wherein the feed comprises or is selected from a waste plastics feed.

Aspect 45. The pyrolysis system or the process for converting plastics to hydrocarbons according to any of the preceding Aspects, wherein the feed is provided to the pyrolysis reactor from an extruder or a liquefier.

Aspect 46. The pyrolysis system or the process for converting plastics to hydrocarbons according to any of the preceding Aspects, wherein the feed comprises or is selected from a plastics feed and the plastics feed is pretreated to remove acid contaminants prior to being provided to the pyrolysis reactor.

Aspect 47. The pyrolysis system or the process for converting plastics to hydrocarbons according to any of the preceding Aspects, wherein the feed comprises or is selected from a plastics feed and the plastics feed is pretreated with caustic, an amine, a zinc alkyl compound, a group II metal, or a combination thereof prior to being provided to the pyrolysis reactor.

Aspect 48. The pyrolysis system or the process for converting plastics to hydrocarbons according to any of Aspects 43-47, wherein the plastics feed is processed through a thin film evaporator to remove volatile acid components prior to being provided to the pyrolysis reactor.

Aspect 49. The pyrolysis system or the process for converting plastics to hydrocarbons according to any of the preceding Aspects, wherein the gaseous pyrolysis reactor effluent is pretreated with caustic, an amine, a metal oxide such as zinc oxide, calcium oxide, or iron oxide, a molecular sieve, or a promoted or activated alumina prior to feeding the gaseous pyrolysis reactor effluent to the condenser system.

Aspect 50. The pyrolysis system or the process for converting plastics to hydrocarbons according to any of the preceding Aspects, wherein the light fraction of the gaseous pyrolysis reactor effluent comprises $C_{\leq 10}$ ($C_{10}$ and lighter) hydrocarbons.

Aspect 51. The pyrolysis system or the process for converting plastics to hydrocarbons according to any of the preceding Aspects, wherein the heavy fraction of the gaseous pyrolysis reactor effluent comprises $C_{\geq 10}$ ($C_{10}$ and heavier) hydrocarbons.

Aspect 52. The pyrolysis system or the process for converting plastics to hydrocarbons according to any of the preceding Aspects, wherein the light fraction gas portion of the light fraction of the gaseous pyrolysis reactor effluent comprises $C_1$ to $C_5$ hydrocarbons.

Aspect 53. The pyrolysis system or the process for converting plastics to hydrocarbons according to any of the preceding Aspects, wherein the light fraction liquid portion of the light fraction of the gaseous pyrolysis reactor effluent comprises $C_5$ to $C_{10}$ hydrocarbons.

Aspect 54. A pyrolysis system for converting plastics to hydrocarbons, the system comprising:

(a) a pyrolysis reactor comprising an inlet to receive a feed, a pyrolysis reactor liquid including a bottoms liquid, a first heater configured to heat the pyrolysis reactor liquid, and an overhead outlet configured to discharge a gaseous pyrolysis reactor effluent;

(b) a condenser system comprising a plurality of condensers in series downstream of the pyrolysis reactor configured to separate the gaseous pyrolysis reactor effluent into a heavy fraction and a light fraction;

(c) a knock-out drum downstream of the condenser system configured to receive the light fraction and separate the light fraction into a light fraction liquid and a light fraction gas; and (d) a gas recycle line from the knock-out drum to the pyrolysis reactor, the gas recycle line comprising a compressor and configured to take off at least a portion of the light fraction gas from the knock-out drum and introduce the compressed light fraction gas through a sparger or a distributor into the pyrolysis reactor liquid at a plurality of gas inlet locations at different heights within pyrolysis reactor.

Aspect 55. A process for converting plastics to hydrocarbons, the process comprising:

(a) providing a plastics feed to a pyrolysis reactor;

(b) pyrolyzing the plastics feed in the pyrolysis reactor to provide (i) a pyrolysis reactor liquid including a bottoms liquid and (ii) a gaseous pyrolysis reactor effluent;

(c) providing the gaseous pyrolysis reactor effluent to a condenser system comprising a plurality of condensers downstream of the pyrolysis reactor and separating the gaseous pyrolysis reactor effluent into a heavy fraction and a light fraction;

(d) providing the light fraction of the gaseous pyrolysis reactor effluent to a knock-out drum downstream of the condenser system and separating the light fraction into a light fraction liquid and a light fraction gas; and (e) compressing and recycling at least a portion of the light fraction gas to the pyrolysis reactor, wherein the compressed light fraction gas is introduced through a sparger or a distributor into the pyrolysis reactor liquid at a plurality of gas inlet locations at different heights within pyrolysis reactor.

What is claimed is:

1. A process for converting plastics to hydrocarbons, the process comprising:
   (a) providing a feed to a pyrolysis reactor;
   (b) pyrolyzing the feed in the pyrolysis reactor to provide (i) a pyrolysis reactor liquid including a bottoms liquid and (ii) a gaseous pyrolysis reactor effluent;
   (c) separating the gaseous pyrolysis reactor effluent into a heavy fraction and a light fraction;
   (d) separating the light fraction of the gaseous pyrolysis reactor effluent into a light fraction liquid and a light fraction gas; and
   (e) recycling at least a portion of the light fraction gas to the pyrolysis reactor, wherein the light fraction gas is introduced into the pyrolysis reactor liquid at a plurality of gas inlet locations.

2. The process according to claim 1, wherein the plurality of gas inlet locations are situated at different heights within the pyrolysis reactor liquid in the pyrolysis reactor.

3. The process according to claim 1, wherein the step of recycling at least a portion of the light fraction gas to the pyrolysis reactor further comprises sparging the light fraction gas into the pyrolysis reactor liquid.

4. The process according to claim 1, wherein the step of recycling at least a portion of the light fraction gas to the pyrolysis reactor further comprises introducing the light fraction gas into the bottoms liquid.

5. The process according to claim 1, further comprising the steps of heating and compressing the light fraction gas prior to recycling the light fraction gas into the pyrolysis reactor liquid.

6. The process according to claim 1, wherein the process further comprises the step of mixing the pyrolysis reactor liquid within the pyrolysis reactor with an internal mixer.

7. The process according to claim 1, wherein the step of separating the gaseous pyrolysis reactor effluent comprises providing the gaseous pyrolysis reactor effluent to a condenser system comprising one or more condensers.

8. The process according to claim 1, wherein the step of separating the gaseous pyrolysis reactor effluent comprises providing the gaseous pyrolysis reactor effluent to a condenser system comprising a plurality of condensers in series.

9. The process according to claim 1, wherein the step of separating the light fraction of the gaseous pyrolysis reactor effluent comprises providing the light fraction of the gaseous pyrolysis reactor effluent to a knock-out drum and separating the light fraction into a light fraction liquid and a light fraction gas.

10. The process according to claim 1, further comprising the step of recycling at least a portion of the bottoms liquid from the pyrolysis reactor into the pyrolysis reactor liquid.

11. The process according to claim 10, wherein the step of recycling at least a portion of the bottoms liquid further comprises heating the bottoms liquid prior to recycling into the pyrolysis reactor liquid.

12. The process according to claim 1, further comprising the step of recycling at least a portion of the heavy fraction of the gaseous pyrolysis reactor effluent into the pyrolysis reactor liquid.

13. The process according to claim 1, further comprising the step of providing the light fraction liquid from the light fraction of the gaseous pyrolysis reactor effluent to a steam cracker furnace to produce a stream cracker furnace effluent comprising ethylene, propylene, and light ($C_1$-$C_5$) saturated hydrocarbons.

14. The process according to claim 13, further comprising the step of separating the steam cracker furnace effluent to provide an ethylene stream.

15. The process according to claim 14, further comprising the step of feeding at least a portion of the ethylene stream to a polymerization reactor to form polyethylene.

16. The process according to claim 1, wherein the feed comprises a waste plastics feed.

17. The process according to claim 16, wherein the waste plastics feed is provided to the pyrolysis reactor from an extruder or a liquefier.

18. The process according to claim 16, wherein the waste plastics feed is pretreated to remove acid contaminants prior to being provided to the pyrolysis reactor.

19. The process according to claim 16, wherein the waste plastics feed is pretreated with caustic, an amine, a zinc alkyl compound, a group II metal, or a combination thereof prior to being provided to the pyrolysis reactor.

20. The process according to claim 16, wherein the waste plastics feed is processed through a thin film evaporator to remove volatile acid components prior to being provided to the pyrolysis reactor.

21. The process according to claim 1, wherein the gaseous pyrolysis reactor effluent is pretreated with caustic, an amine, a metal oxide, a molecular sieve, or a promoted or activated alumina prior to feeding the gaseous pyrolysis reactor effluent to the condenser system.

22. The process according to claim 21, wherein the metal oxide is selected from zinc oxide, calcium oxide, or iron oxide.

23. A process for converting plastics to hydrocarbons, the process comprising:
   (a) providing a plastics feed to a pyrolysis reactor;
   (b) pyrolyzing the plastics feed in the pyrolysis reactor to provide (i) a pyrolysis reactor liquid including a bottoms liquid and (ii) a gaseous pyrolysis reactor effluent;
   (c) providing the gaseous pyrolysis reactor effluent to a condenser system comprising a plurality of condensers downstream of the pyrolysis reactor and separating the gaseous pyrolysis reactor effluent into a heavy fraction and a light fraction;
   (d) providing the light fraction of the gaseous pyrolysis reactor effluent to a knock-out drum downstream of the condenser system and separating the light fraction into a light fraction liquid and a light fraction gas; and
   (e) compressing and recycling at least a portion of the light fraction gas to the pyrolysis reactor, wherein the compressed light fraction gas is introduced through a sparger or a distributor into the pyrolysis reactor liquid at a plurality of gas inlet locations at different heights within pyrolysis reactor.

24. A pyrolysis system for converting plastics to hydrocarbons, the system comprising:
   (a) a pyrolysis reactor comprising an inlet configured to receive a feed, a pyrolysis reactor liquid including a bottoms liquid, a first heater configured to heat the pyrolysis reactor liquid, and an overhead outlet configured to discharge a gaseous pyrolysis reactor effluent;
   (b) a condenser system comprising one or more condensers downstream of the pyrolysis reactor configured to separate the gaseous pyrolysis reactor effluent into a heavy fraction and a light fraction;
   (c) a knock-out drum downstream of the condenser system configured to receive the light fraction from the condenser system and separate the light fraction into a light fraction liquid and a light fraction gas; and (d) a gas recycle line configured to take off at least a portion of the light fraction gas from the knock-out drum and recycle the light fraction gas into the pyrolysis reactor liquid at a plurality of gas inlet locations situated at different heights within the pyrolysis reactor liquid.

25. The pyrolysis system according to claim 24, wherein the pyrolysis system further comprises a bottoms liquid recycle line comprising a first pump and configured to take off at least a portion of the bottoms liquid from the pyrolysis reactor and recycle the bottoms liquid into the pyrolysis reactor liquid wherein the bottoms liquid recycle line further comprises a second heater to heat the bottoms liquid prior to recycling.

26. The pyrolysis system according to claim 24, wherein the gas recycle line comprises a sparger or a distributor at the termination of each of the plurality of gas inlet locations of the gas recycle line within the pyrolysis reactor liquid.

27. The pyrolysis system according to claim 24, wherein the gas recycle line is configured to introduce the light fraction gas into the bottoms liquid.

28. The pyrolysis system according to claim 24, wherein the gas recycle line comprises (a) a compressor between the knock-out drum and pyrolysis reactor to compress the light fraction gas and (b) a third heater to heat the light fraction gas prior to recycling the light fraction gas into the pyrolysis reactor liquid.

29. The pyrolysis system according to claim 24, wherein the first heater comprises or is selected from an external heating jacket.

30. The pyrolysis system according to claim 24, wherein the pyrolysis reactor further comprises an internal mixer configured to mix the pyrolysis reactor liquid within the pyrolysis reactor.

31. The pyrolysis system according to claim 24, wherein the condenser system comprises a plurality of condensers in series.

32. The pyrolysis system according to claim 24, wherein the pyrolysis system further comprises a heavy fraction recycle line comprising a second pump and configured to recycle at least a portion of the heavy fraction of the gaseous pyrolysis reactor effluent from the condenser system into the pyrolysis reactor liquid.

33. A pyrolysis system for converting plastics to hydrocarbons, the system comprising:
(a) a pyrolysis reactor comprising an inlet to receive a feed, a pyrolysis reactor liquid including a bottoms liquid, a first heater configured to heat the pyrolysis reactor liquid, and an overhead outlet configured to discharge a gaseous pyrolysis reactor effluent;
(b) a condenser system comprising a plurality of condensers in series downstream of the pyrolysis reactor configured to separate the gaseous pyrolysis reactor effluent into a heavy fraction and a light fraction;
(c) a knock-out drum downstream of the condenser system configured to receive the light fraction and separate the light fraction into a light fraction liquid and a light fraction gas; and
(d) a gas recycle line from the knock-out drum to the pyrolysis reactor, the gas recycle line comprising a compressor and configured to take off at least a portion of the light fraction gas from the knock-out drum and introduce the compressed light fraction gas through a sparger or a distributor into the pyrolysis reactor liquid at a plurality of gas inlet locations at different heights within pyrolysis reactor.

* * * * *